United States Patent
Murayama et al.

(10) Patent No.: US 10,035,767 B2
(45) Date of Patent: Jul. 31, 2018

(54) METHOD FOR PRODUCING SYNTHETIC PENTAPEPTIDE

(71) Applicant: MARUISHI PHARMACEUTICAL CO., LTD., Osaka-shi (JP)

(72) Inventors: Asami Murayama, Chuo-ku (JP); Takaaki Kano, Chuo-ku (JP)

(73) Assignee: MARUISHI PHARMACEUTICAL CO., LTD., Osaka-shi (JP)

( * ) Notice: Subject to any disclaimer, the term of this patent is extended or adjusted under 35 U.S.C. 154(b) by 43 days.

(21) Appl. No.: 15/320,488

(22) PCT Filed: Dec. 19, 2014

(86) PCT No.: PCT/JP2014/083651
§ 371 (c)(1),
(2) Date: Dec. 20, 2016

(87) PCT Pub. No.: WO2015/198505
PCT Pub. Date: Dec. 30, 2015

(65) Prior Publication Data
US 2017/0183307 A1    Jun. 29, 2017

(30) Foreign Application Priority Data
Jun. 26, 2014 (JP) .................. 2014-130891

(51) Int. Cl.
C07D 211/56 (2006.01)
C07D 211/28 (2006.01)
C07D 211/02 (2006.01)
C07K 1/12 (2006.01)

(52) U.S. Cl.
CPC .......... *C07D 211/56* (2013.01); *C07D 211/02* (2013.01); *C07D 211/28* (2013.01); *C07K 1/128* (2013.01)

(58) Field of Classification Search
None
See application file for complete search history.

(56) References Cited

U.S. PATENT DOCUMENTS

| | | |
|---|---|---|
| 7,402,564 B1 | 7/2008 | Schteingart et al. |
| 8,217,007 B1 | 7/2012 | Schteingart et al. |
| 2009/0075907 A1 | 3/2009 | Schteingart et al. |
| 2009/0156508 A1 | 6/2009 | Schteingart et al. |
| 2009/0264373 A1 | 10/2009 | Schteingart et al. |
| 2010/0075910 A1 | 3/2010 | Schteingart et al. |
| 2010/0226597 A1* | 9/2010 | Palle ........... C07F 5/025 383/113 |
| 2011/0118186 A1 | 5/2011 | Schteingart et al. |
| 2011/0212882 A1 | 9/2011 | Schteingart et al. |
| 2011/0257105 A1 | 10/2011 | Schteingart et al. |
| 2013/0012448 A1 | 1/2013 | Schteingart et al. |
| 2014/0357579 A1 | 12/2014 | Schteingart et al. |
| 2015/0197545 A1 | 7/2015 | Schteingart et al. |
| 2016/0362450 A1 | 12/2016 | Schteingart et al. |

FOREIGN PATENT DOCUMENTS

| | | |
|---|---|---|
| JP | 2010-510966 A | 4/2010 |
| JP | 2013-241447 A | 12/2013 |
| WO | WO 2008/057608 A2 | 5/2008 |

OTHER PUBLICATIONS

International Search Report dated Mar. 17, 2015 in PCT/JP2014/083651 filed Dec. 19, 2014.
Albericio, F., "Orthogonal Protecting Groups for N(alpha)-Amino and C-Terminal Carboxyl Functions in Solid-Phase Peptide Synthesis," Biopolymers, vol. 55, 2000, pp. 123-139, (17 pages).
Takahashi, D. et al., "Novel diphenylmethyl-Derived Amide Protecting Group for Efficient Liquid-Phase Peptide Synthesis: AJIPHASE," Organic Letters, vol. 14, No. 17, 2012, pp. 4514-4517, (4 pages).
Shumpei, Sakakibara, "Chemical Synthesis of Protein: Protein, Nucleic Acid, Enzyme," From Chemistry to Biology: Present and Future of Protein Research, vol. 40, No. 3, 1995, pp. 304-316, (16 pages, with Partial English Translation).
Extended Search Report dated Jan. 4, 2018 in European Patent Application No. 14896077.6.

* cited by examiner

Primary Examiner — Marcela M Cordero Garcia
Assistant Examiner — Jia-Hai Lee
(74) Attorney, Agent, or Firm — Oblon, McClelland, Maier & Neustadt, L.L.P.

(57) ABSTRACT

Provided are a method for industrially advantageously producing a highly purified pentapeptide and an intermediate thereof.
A compound represented by the following formula (1) or a salt thereof:

(1)

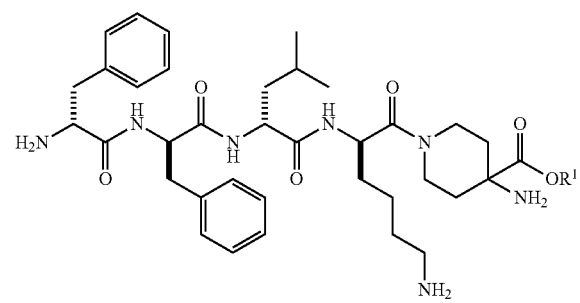

wherein $R^1$ represents an alkyl group or an aralkyl group.

18 Claims, No Drawings

METHOD FOR PRODUCING SYNTHETIC PENTAPEPTIDE

FIELD OF THE INVENTION

The present invention relates to a method for producing a synthetic pentapeptide and to an intermediate thereof.

BACKGROUND OF THE INVENTION

It is known that κ opioid receptor agonists are useful as therapeutic agents for various types of pain. Of them, a κ opioid receptor agonist having high selectivity to a peripheral κ opioid receptor is expected as a medicine producing no side effects on the central nervous system. As such a peripherally-selective κ opioid receptor agonist, synthetic pentapeptides have been reported (Patent Literatures 1 and 2).

Of the synthetic pentapeptides, a compound represented by the following formula (A):

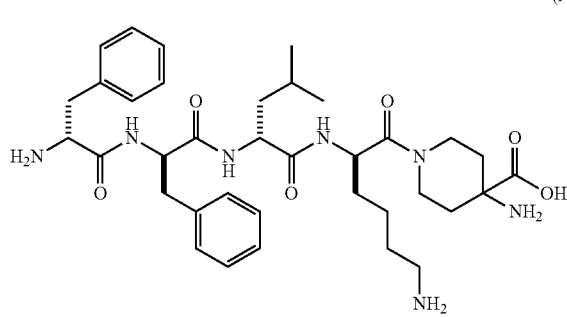

(A)

is useful as a therapeutic agent for pain. As a method for producing this compound, Patent Literatures 1 and 2 mentioned above describe a solid-phase peptide synthesis method.

CITATION LIST

Patent Literature

[Patent Literature 1] JP-A-2010-510966
[Patent Literature 2] JP-A-2013-241447

SUMMARY OF THE INVENTION

Technical Problem

However, in the production by the solid-phase peptide synthesis method, a pentapeptide with protecting groups is synthesized, and then removal from a resin and removal of all protecting groups are carried out, followed by purification by preparative HPLC. The purification requires a large-scale preparative HPLC apparatus and takes long time. In contrast, a peptide can be synthesized by a liquid-phase method. However, when a pentapeptide having protection groups in an intermediate step was deprotected and then purified to obtain a compound (A), the purity of the resultant compound (A) was less than 80%. From this, it was found that a highly pure compound (A) is not obtained.

Accordingly, a technical problem to be solved by the present invention is to provide a method for industrially advantageously producing a highly pure compound (A).

Solution to Problem

The present inventors conducted studies on a method for producing a highly pure compound (A). When they isolated the following compound (1) by removing only an N-protecting group from a compound (A) having N- and O-protecting groups, it was wholly surprisingly found that a highly pure compound (1) can be obtained through purification by a slurry method and a recrystallization method; and that if the compound (1) is hydrolyzed, a compound (A) having a purity as high as 90% or more can be industrially advantageously produced. Based on the findings, the present invention was accomplished.

The present invention further provides the following [1] to [4].

[1] A compound represented by the following formula (1) or a salt thereof:

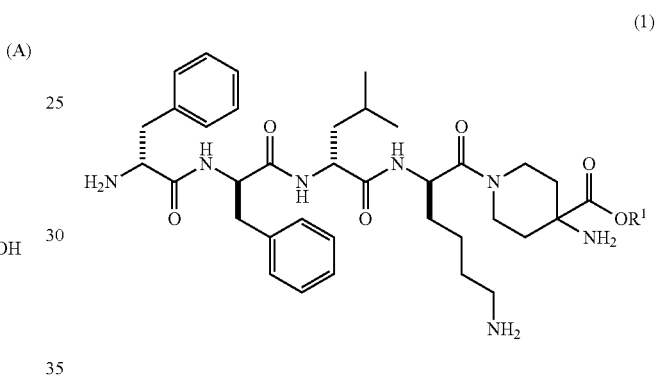

(1)

wherein $R^1$ represents an alkyl group or an aralkyl group.

[2] The compound or a salt thereof according to [1], wherein $R^1$ is an alkyl group.

[3] The compound or a salt thereof according to [1] or [2], wherein the compound or a salt thereof is an acid addition salt of the compound.

[4] A method of producing a compound represented by formula (A) or a salt thereof:

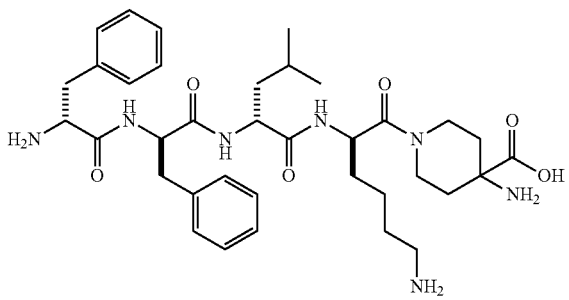

(A)

comprising hydrolyzing the compound or a salt thereof according to any one of [1] to [3]

Effects of Invention

A compound (1) can be purified by a simple operation and if the compound (1) is hydrolyzed, a highly pure compound (A) can be industrially advantageously produced.

DESCRIPTION OF EMBODIMENTS

A compound (1) of the present invention or a salt thereof is useful as an intermediate for synthesizing a compound (A).

In the formula (1), $R^1$ represents an alkyl group or an aralkyl group. Examples of the alkyl group include linear or branched alkyl groups having 1 to 12 carbon atoms. Of them, a linear or branched alkyl group having 1 to 8 carbon atoms is preferable and a linear or branched alkyl group having 1 to 4 carbon atoms is more preferable. Examples of the alkyl group include a methyl group, an ethyl group, a n-propyl group, an isopropyl group, a n-butyl group and a tert-butyl group. A methyl group is further preferable.

As the aralkyl group, an aralkyl group having 7 to 18 carbon atoms is preferable; a $C_{6-14}$ aryl-$C_{1-4}$ alkyl group is more preferable; a phenyl-$C_{1-4}$ alkyl group is even more preferable; and a benzyl group is further preferable.

Of the groups represented by $R^1$, an alkyl group is preferable; a $C_{1-6}$ alkyl group is more preferable; a $C_{1-4}$ alkyl group is even more preferable; and a methyl group is further preferable.

As a salt of a compound (1), an acid addition salt is mentioned. Specific examples of the acid addition salt include inorganic acid salts such as a hydrochloride, a sulfate and a nitrate; and organic acid salts such as an acetate, and a trifluoroacetate. A hydrochloride is preferable as the inorganic acid salt; and a trifluoroacetate is preferable as the organic acid salt. Of them, a hydrochloride is more preferable.

Of the compounds (1) and salts thereof, a salt of a compound (1) wherein $R^1$ is a $C_{1-6}$ alkyl group is preferable since the salt can be easily isolated in the form of a crystal and easily purified; an acid addition salt of a compound (1) wherein $R^1$ is a $C_{1-6}$ alkyl group is more preferable; an acid addition salt of a compound (1) wherein $R^1$ is a $C_{1-4}$ alkyl group is even more preferable; and an acid addition salt of a compound (1) wherein $R^1$ is a methyl group is further preferable.

A compound (1) or a salt thereof and a compound (A) can be produced by a liquid-phase peptide synthesis method in which 4-aminopiperidine-4-carboxylic acid, D-lysine (D-Lys), D-leucine (D-Leu), D-phenylalanine (D-Phe) and D-phenylalanine (D-Phe) are subsequently condensed, as shown, for example, in the following reaction scheme.

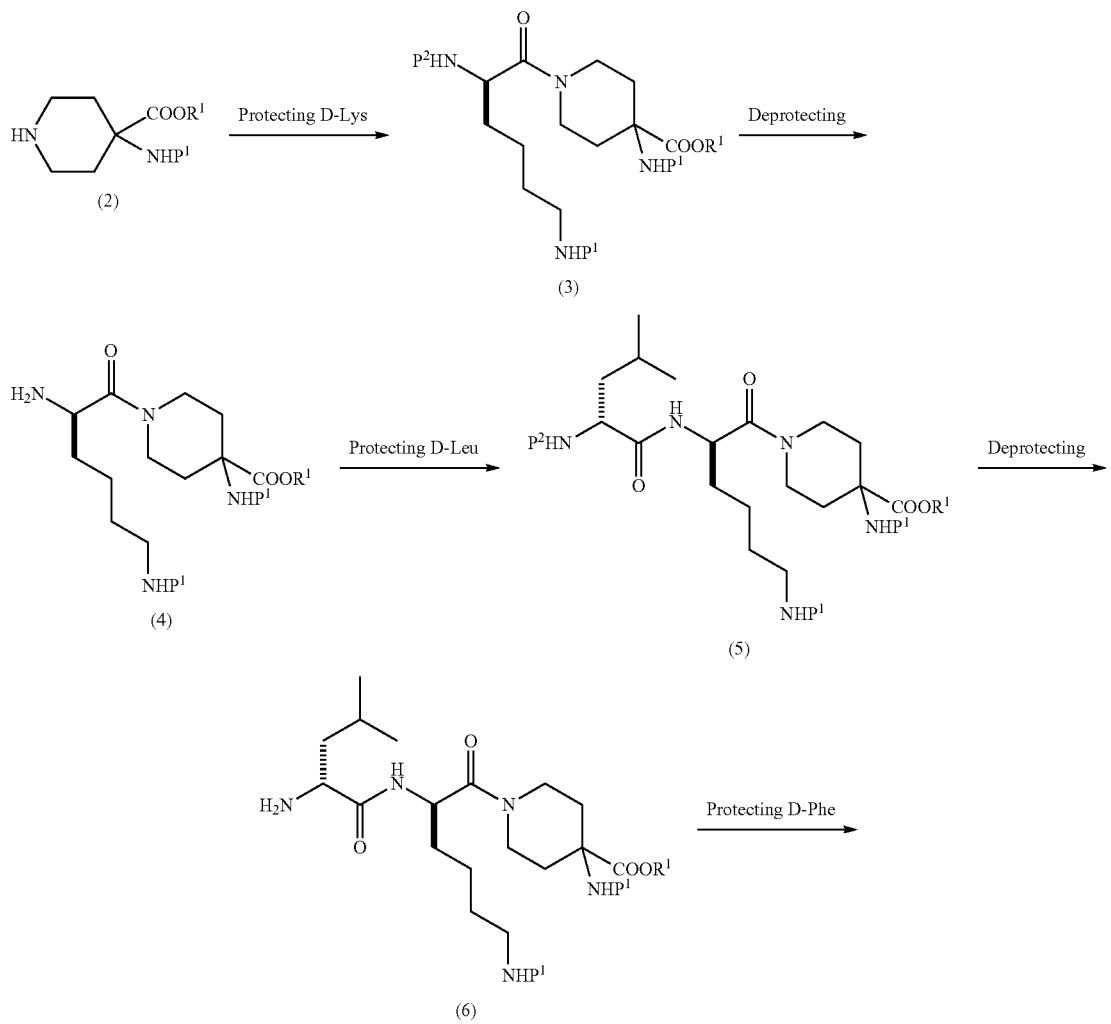

-continued
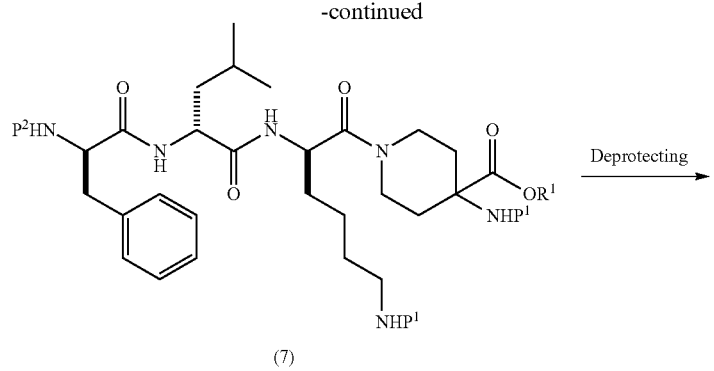
(7)
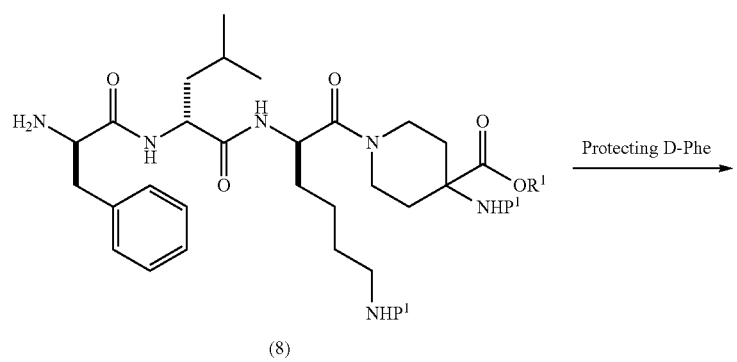
(8)
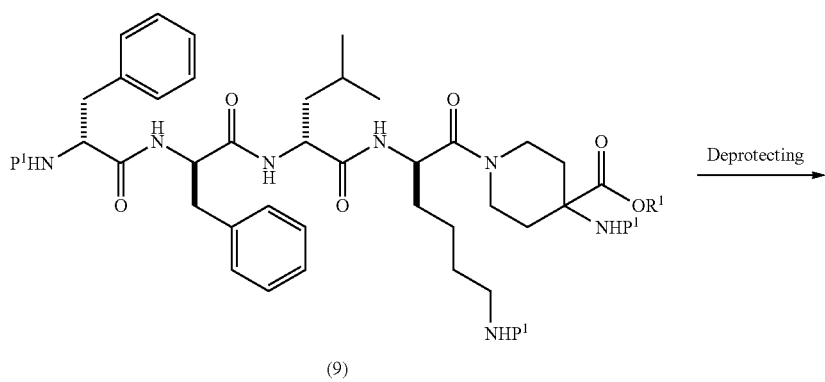
(9)
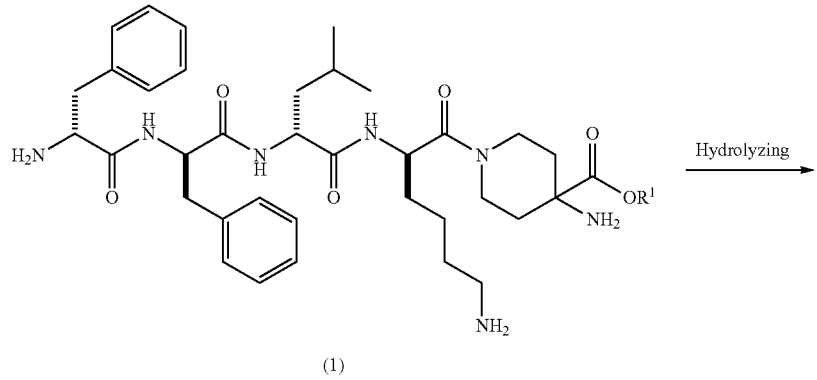
(1)

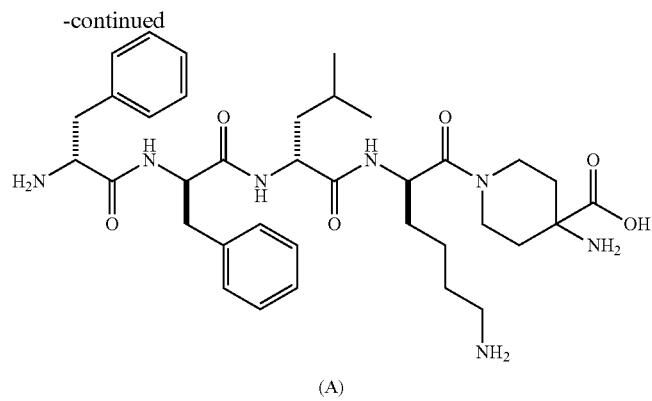

(A)

where $P^1$ and $P^2$ each represent an N-protecting group and $R^1$ is the same as defined above.

In the above reaction scheme, it is preferable that the N-protecting groups represented by $P^1$ and $P^2$ are protecting groups which can be separately removed by different removal means. Examples of these protecting groups include (1) protecting groups which can be removed with an acid (for example, a tert-butoxycarbonyl group (Boc), a p-methoxybenzyloxycarbonyl group (Moz), a formyl group (CHO), a 2-(trimethylsilyl)ethoxycarbonyl group (Teoc), a 1-adamantyloxycarbonyl group (Adoc), a 2-(p-biphenyl)isopropyloxycarbonyl group (Bpoc), a triphenylmethyl group (Tr), a methoxymethyl group (MOM)); (2) protecting groups which can be removed by reduction (for example, a benzyloxycarbonyl group (Cbz), an allyl group (Allyl), a N-benzyloxymethyl group (BOM)); (3) protecting groups which can be removed with a secondary amine (for example, a 9-fluorenylmethyloxycarbonyl group (Fmoc), a 2-(4-nitrophenyl)ethoxycarbonyl group (Npeoc)); (4) protecting groups which can be removed with e.g., a zinc powder-acetic acid (for example, a 2,2,2-trichloroethoxycarbonyl group (Troc), a N-dithiasuccinoyl group (Dts), a benzothiazol-2-sulfonyl group (Betsyl), a 1,1-dimethyl-2,2,2-trichloroethoxy carbonyl group (TcBoc), a N-(diphenyl-4-pyridyl)methyl group (Dppm)); and (5) protecting groups which can be removed with e.g., an amine in the presence of a palladium catalyst (for example, an allyloxycarbonyl group (Alloc)). As $P^1$ and $P^2$, protecting groups which can be removed in different conditions may be selected from these protecting groups and used. For example, Boc is preferable as $P^1$ and Cbz is preferable as $P^2$.

The condensation reactions between a compound (2) and protected D-Leu; between a compound (4) and protected D-Leu; between a compound (6) and protected D-Phe; and between a compound (8) and protected D-Phe can be carried out in the presence of a condensing agent such as a molecular sieve, 1-hydroxybenzotriazole (HOBt), 1-ethyl-3-(3-dimethylaminopropyl)carbodiimide hydrochloride (EDC.HCl) and N,N-dicyclohexylcarbodiimide (DCC); and more specifically, in a solvent such as a halogen, ester or ether solvent, in the presence of a condensing agent, at a temperature of 0 to 40° C. for 1 to 48 hours.

The deprotection reaction can be carried out by selecting an appropriate method depending upon the type of protecting group. To obtain a compound (1) in the form of an acid addition salt such as a hydrochloride, it is preferable that a protecting group (for example, Boc) which can be removed with an acid is selected as $P^1$ and a protecting group (for example, (Cbz)) which can be removed by reduction is selected as $P^2$. When Boc is used as $P^1$, if $P^1$ is removed, for example, by hydrolysis using an acid, an acid addition salt of a compound (1) can be obtained. Deprotection by reduction can be carried out, for example, by a reaction in a solvent such as an ester solvent or an ether solvent in the presence of a metal catalyst at 0 to 40° C. for 1 to 48 hours. Deprotection with an acid can be carried out in a solvent such as an ester solvent or an ether solvent, in the presence of e.g., an inorganic acid or a trifluoroacetic acid at 0 to 40° C. for 1 to 48 hours.

A salt of a compound (1) can be easily purified by e.g., recrystallization. A salt of a compound (1) has a sufficiently high purity even if it is not purified. Accordingly, a highly pure compound (A) can be produced by hydrolysis of a salt of a compound (1). The hydrolysis reaction herein is preferably carried out in the presence of e.g., a base; and more specifically, can be carried out in the presence of e.g., sodium hydroxide in e.g., water or an alcohol-based solvent at 0 to 40° C. for 1 to 48 hours.

In the method for producing a compound (A) according to the method (liquid-phase method) of the present invention, impurities difficult to remove, such as diastereomers and defective peptide, are rarely produced unlike a solid-phase synthesis method, and even if produced, the impurities can be removed in an intermediate step. In addition, since an intermediate compound can be isolated unlike a solid-phase synthesis method, a filtration purification method, which is a relatively easy operation requiring no expensive equipment investment, such as a slurry method and a recrystallization method, can be used, with the result that a desired product having a high purity of 99% (value measured by e.g., HPLC) is easily obtained.

Unlike the solid-phase synthesis method where the solvent to be used is limited to e.g., methylene chloride and dimethylformamide; a safe and inexpensive solvent suitable for industrialization can be used in the liquid-phase synthesis. A large amount of product is easily synthesized unlike the solid-phase synthesis method. In the solid-phase synthesis method, "preparative HPLC" (generally expensive equipment and a large amount of organic solvent are required) is often used for purification of a final compound; however, these problems can be avoided in the liquid-phase synthesis.

EXAMPLES

The present invention will be more specifically described below by way of Examples.

Example 1

(1) Synthesis of Cbz-D-Lys(Boc)-α-Boc-Pic-OMe (3)

A four-necked flask (2L) was charged with α-Boc-Pic-OMe.HCl[methyl α-Boc-4-aminopiperidine-4-carboxylate hydrochloride] (2) (43.7 g (148 mmol)), which was suspended in EtOAc (656 mL (15 v/w)). To the suspension solution, 1-hydroxybenzotriazole (HOBt) (27.2 g (178 mmol)) and Cbz-D-Lys(Boc)-OH (59.2 g (156 mmol)) were added. While cooling the flask in an ice bath, 1-ethyl-3-(3-dimethylaminopropyl) carbodiimide.HCl (EDC.HCl) (34.1 g (178 mmol)) was added. Twenty minutes later, the temperature of the mixture was increased to room temperature and the mixture was stirred for 12 hours. After completion of the reaction, 1N HCl (218 mL (5.0 v/w)) was added to separate an organic layer. To the obtained organic layer, NaHCO$_3$ aq. (218 mL (5.0 v/w)) and Et$_3$N (33.0 g (326 mmol)) were added. The mixture was stirred for 30 minutes to separate layers. The organic layer was washed sequentially with 1N HCl (218 mL (5.0 v/w)), NaHCO$_3$ aq. (218 mL (5.0 v/w)) and NaCl aq. (218 mL (5.0 v/w)), dried by adding Na$_2$SO$_4$ (8.74 g (0.2 w/w)) and filtered under reduced pressure. The resultant filtrate was concentrated under reduced pressure by an evaporator, and pumped up by a vacuum pump to obtain Cbz-D-Lys(Boc)-α-Boc-Pic-OMe (3) (88.9 g) as a white solid (yield 96.5%, HPLC purity 96.5%).

(2) Synthesis of D-Lys(Boc)-α-Boc-Pic-OMe (4)

A 2 L-recovery flask was charged with Cbz-D-Lys(Boc)-α-Boc-Pic-OMe (3) (88.3 g (142 mmol)), which was dissolved by adding EtOAc (441 mL (5.0 v/w)). To the reaction solution, 5% Pd/C (17.7 g (0.2 w/w)) was added and replacement of the air in the flask by nitrogen gas was carried out three times under a reduced-pressure atmosphere, followed by replacement by hydrogen gas three times. The reaction solution was vigorously stirred at room temperature for 18 hours. After completion of the reaction, the reaction solution was filtered under reduced pressure to remove Pd/C. To the resultant filtrate, NaHCO$_3$ aq. (441 mL (5.0 v/w)) was added to separate layers. To the aqueous layer, EtOAc (200 mL (2.3 v/w)) was added and the organic layer was extracted. The organic layers extracted in this manner were combined and NaHCO$_3$ aq. (441 mL (5.0 v/w)) was added thereto and separate layers. To the obtained aqueous layer, EtOAc (200 mL (2.3 v/w)) was added and the organic layer was extracted. The organic layers obtained in this manner were combined and NaCl aq. (441 mL (5.0 v/w)) was added thereto to separate layers. To the obtained aqueous layer, EtOAc (200 mL (2.3 v/w)) was added and extraction was made. The organic layers obtained in this manner were combined, dried by adding Na$_2$SO$_4$ (17.7g (0.2 w/w)) thereto and filtered under reduced pressure. The obtained filtrate was concentrated under reduced pressure by an evaporator and pumped up by a vacuum pump to obtain D-Lys(Boc)-α-Boc-Pic-OMe (4) (62.7 g) (yield 90.5%, HPLC purity 93.6%).

(3) Synthesis of Cbz-D-Leu-D-Lys(Boc)-α-Boc-Pic-OMe (5)

A four-necked flask (2 L) was charged with D-Lys(Boc)-α-Boc-Pic-OMe (4) (57.7 g (120 mmol)), which was suspended in EtOAc (576 mL (10 v/w)). To the suspension solution, HOBt (19.3 g (126 mmol)) and Cbz-D-Leu-OH (33.4 g (126 mmol)) were added. While the flask was cooled in an ice bath, EDC.HCl (24.2 g (126 mmol)) was added. Twenty minutes later, the temperature of the mixture was increased to room temperature and the mixture was stirred for 5 hours. To the mixture, further EDC.HCl (1.15 g (6.00 mmol)) was added and stirred for 16 hours. After completion of the reaction, 1N HCl (576 mL (10 v/w)) was added to separate layers. To the obtained organic layer, NaHCO$_3$ aq. (576 mL (10 v/w)) and Et$_3$N (24.3 g (240 mmol)) were added and stirred for 30 minutes to separate layers. The organic layer was washed sequentially with 1N HCl (576 mL (10 v/w)), NaHCO$_3$ aq. (576 mL (10 v/w)) and NaCl aq. (576 mL (10 v/w)), dried by adding Na$_2$SO$_4$ (11.5 g (0.2 w/w)), and filtered under reduced pressure. The resultant filtrate was concentrated under reduced pressure by an evaporator and pumped up by a vacuum pump to obtain Cbz-D-Leu-D-Lys(Boc)-α-Boc-Pic-OMe (5) (85.8 g) as a white solid (yield 98.7%, HPLC purity 96.9%).

(4) Synthesis of D-Leu-D-Lys(Boc)-α-Boc-Pic-OMe (6)

A 1 L-recovery flask was charged with Cbz-D-Leu-D-Lys(Boc)-α-Boc-Pic-OMe (5) (91.9 g (125 mmol)), which was dissolved by adding EtOAc (459 mL (5.0 v/w)). To the reaction solution, 5% Pd/C (18.4 g (0.2 w/w)) was added and replacement of the air in the flask by nitrogen gas was carried out three times under a reduced-pressure atmosphere, followed by replacement by hydrogen gas three times. The reaction solution was vigorously stirred at room temperature for 8 hours. After completion of the reaction, the reaction solution was filtered under reduced pressure to remove Pd/C. To the resultant filtrate, NaHCO$_3$ aq. (200 mL (2.2 v/w)) was added to separate layers. To the organic layer, NaHCO$_3$ aq. (200 mL (2.2 v/w)) and NaCl aq. (200 mL (2.2 v/w)) were sequentially added to wash the organic layer. The obtained organic layer was dried by adding Na$_2$SO$_4$ (18.4 g (0.2 w/w)) thereto and filtered under reduced pressure. The resultant filtrate was concentrated under reduced pressure by an evaporator and pumped up by a vacuum pump. The obtained amorphous solid was dissolved by adding EtOAc (200 mL (2.2 v/w)) and crystallized by adding heptane (50 mL (1.8 v/w)). The precipitated crystal was separated by filtration under reduced pressure and washed with a solvent mixture of EtOAc (120 mL (1.3 v/w)) and heptane (50 mL (0.3 v/w)). The obtained crystal (46.1 g) was dissolved by adding EtOAc (480 mL (5.2 v/w)) and crystallized by adding cyclohexane 660 mL (7.2 v/w). The precipitated crystal was separated by filtration under reduced pressure, washed with a solvent mixture of cyclohexane (120 mL (1.3 v/w)) and EtOAc (20 mL (0.2 v/w)) and dried at 30° C. under reduced pressure to obtain D-Leu-D-Lys(Boc)-α-Boc-Pic-OMe (6) (36.6 g) as a white solid (yield 48.7%, HPLC purity 99.9%.

(5) Synthesis of Cbz-D-Phe-D-Leu-D-Lys(Boc)-α-Boc-Pic-OMe (7)

A four-necked flask (1 L) was charged with D-Leu-D-Lys(Boc)-α-Boc-Pic-OMe (6) (35.8 g (59.6 mmol)), which was suspended in EtOAc (358 mL (10 v/w)). To the suspension solution, HOBt (9.59 g (62.6 mmol)) and Cbz-D-Phe-OH (18.7 g (62.6 mmol)) was added. While the flask was cooled in an ice bath, EDC.HCl (12.0 g (62.6 mmol)) was added. Twenty minutes later, the temperature of the mixture was increased to room temperature and the mixture was stirred for 16 hours and further EDC.HCl (3.09 g (16.1 mmol)) was added. After completion of the reaction, 1N HCl (358 mL (10 v/w)) was added and the organic layer was separated. To the obtained organic layer, NaHCO$_3$ aq. (358 mL (10 v/w)) and Et$_3$N (12.1 g (119 mmol)) were added and the mixture was stirred for 30 minutes to separate layers. The organic layer was washed sequentially with 1N HCl (358 mL (10 v/w)), NaHCO₃ aq. (358 mL (10 v/w)) and NaCl aq. (358 mL (10 v/w)), dried by adding Na₂SO₄ (7.16 g (0.2 w/w)) and filtered under reduced pressure. The resultant filtrate was concentrated under reduced pressure by an evaporator and pumped up by a vacuum pump to obtain Cbz-D-Phe-D-Leu-D-Lys(Boc)-α-Boc-Pic-OMe (7) (52.5 g) as a white solid (yield quant, HPLC purity 97.6%).

(6) Synthesis of D-Phe-D-Leu-D-Lys(Boc)-α-Boc-Pic-OMe (8)

A 2L-recovery flask was charged with Cbz-D-Phe-D-Leu-D-Lys(Boc)-α-Boc-Pic-OMe (7) (46.9 g (53.3 mmol)), which was dissolved by adding EtOAc (840 mL (18 v/w)) and H₂O (93.8 mL (2.0 v/w)). To the reaction solution, 5% Pd/C (9.38 g (0.2 w/w)) was added, replacement of the air in the flask by nitrogen gas was carried out three times under a reduced-pressure atmosphere, followed by replacement by hydrogen gas three times. The reaction solution was vigorously stirred at room temperature for 10 hours. After completion of the reaction, the reaction solution was filtered under reduced pressure to remove Pd/C. To the resultant filtrate, NaHCO₃ aq. (235 mL (5.0 v/w)) was added to separate layers. To the organic layer, NaHCO₃ aq. (235 mL (5.0 v/w)) and NaCl aq. (235 mL (5.0 v/w)) were sequentially added to wash the organic layer. The obtained organic layer, was dried by adding Na₂SO₄ (9.38 g (0.2 w/w)) thereto and filtered under reduced pressure. The resultant filtrate was concentrated under reduced pressure by an evaporator and pumped up by a vacuum pump to obtain D-Phe-D-Leu-D-Lys(Boc)-α-Boc-Pic-OMe (8) (39.7 g) (yield quant, HPLC purity 97.3%).

(7) Synthesis of Boc-D-Phe-D-Phe-D-Leu-D-Lys(Boc)-α-Boc-Pic-OMe (9)

A four-necked flask (1 L) was charged with D-Phe-D-Leu-D-Lys(Boc)-α-Boc-Pic-OMe (8) (35.1 g), which was suspended by adding EtOAc (351 mL (10 v/w)). To the suspension solution, HOBt (7.92 g (51.7 mmol)) and Boc-D-Phe-OH (13.1 g (49.4 mmol)) were added. While cooling the flask in an ice bath, EDC.HCl (9.91 g (51.7 mmol)) was added. Twenty minutes later, the temperature of the mixture was increased to room temperature and the mixture was stirred for 8 hours and further EDC.HCl (2.25 g (11.7 mmol)) was added. After completion of the reaction, 1N HCl (351 mL (10 v/w)) was added to separate an organic layer. To the obtained organic layer, NaHCO₃ aq. (351 mL (10 v/w)) and Et₃N (9.51g (94.0 mmol)) were added. The mixture was stirred for 30 minutes to separate layers. The organic layer was washed sequentially with 1N HCl (351 mL (10 v/w)), NaHCO₃ aq. (351 mL (10 v/w)) and NaCl aq. (351 mL (10 v/w)), dried by adding Na₂SO₄ (7.02 g (0.2 w/w)) and filtered under reduced pressure. The resultant filtrate was concentrated under reduced pressure by an evaporator and pumped up by a vacuum pump to obtain Boc-D-Phe-D-Phe-D-Leu-D-Lys(Boc)-α-Boc-Pic-OMe (9) (46.7 g) as a white solid (yield quant, HPLC purity 98.6%).

(8) Synthesis of D-Phe-D-Phe-D-Leu-D-Lys-Pic-OMe hydrochloride (1)

A 20 mL-recovery flask was charged with Boc-D-Phe-D-Phe-D-Leu-D-Lys(Boc)-α-Boc-Pic-OMe (9) (2.00 g), which was suspended by adding IPA (3.3 mL (1.65 v/w)) and PhMe (10 mL (5 v/w)). To the mixture, 6N HCl/IPA (6.7 mL (3.35 v/w)) was added and stirred at room temperature for 19 hours. The precipitated solid was separated by filtration under reduced pressure and dried under reduced pressure to obtain D-Phe-D-Phe-D-Leu-D-Lys-Pic-OMe hydrochloride (1) (1.59 g) as a white solid (yield 99.0%, HPLC purity 98.2%).

(9) Purification of D-Phe-D-Phe-D-Leu-D-Lys-Pic-OMe hydrochloride (1)

A 20 mL-recovery flask was charged with a crude crystal of D-Phe-D-Phe-D-Leu-D-Lys-Pic-OMe hydrochloride (1) (200 mg), to which a solvent mixture (4.0 mL (20 v/w)) containing EtOH: MeCN in a ratio of 1:5 was added. The mixture was heated to 40° C. and stirred for one hour and further stirred at room temperature for two hours to obtain slurry. The mixture was separated by filtration under reduced pressure and the resultant solid was dried under reduced pressure to obtain a white solid ((1) purified crystal) (161 mg) (yield 80%, HPLC purity 99.2%).

(10) Synthesis of D-Phe-D-Phe-D-Leu-D-Lys-Pic (A) (purified crystal (1) was used)

A 10 mL-recovery flask was charged with a purified crystal of D-Phe-D-Phe-D-Leu-D-Lys-Pic-OMe hydrochloride (1) (38.5 mg (0.0488 mmol)), which was dissolved by adding H₂O (0.2 mL (5.2 v/w)). To the mixture, 1N NaOH (197 µL (0.197 mmol)) was added dropwise at room temperature and stirred for 1.5 hours. After completion of the reaction, 1N HCl (48.8 µL (0.0488 mmol)) was added and the resultant mixture was concentrated under reduced pressure by an evaporator to obtain D-Phe-D-Phe-D-Leu-D-Lys-Pic (A) (yield quant, HPLC purity 99.7%).

Physical properties of D-Phe-D-Phe-D-Leu-D-Lys-Pic-OMe (1)

¹H NMR (400 MHz, 1M DCl) δ ppm: 0.85-1.02 (m, 6 H), 1.34-1.63 (m, 5 H), 1.65-2.12 (m, 5 H), 2.23-2.45 (m, 2 H), 2.96-3.12 (m, 4 H), 3.19 (ddt, J=5.0 & 5.0 & 10.0 Hz), 3.33-3.62 (m, 1 H), 3.68-3.82 (m, 1 H), 3.82-3.95 (m, 4 H), 3.95-4.18 (m, 1 H), 4.25-4.37 (m, 2 H), 4.61-4.77 (m, 2 H), 7.21-7.44 (m, 10 H)

¹³C NMR (400 MHz, 1M DCl) δ ppm: 21.8, 22.5, 24.8, 27.0, 30.5, 30.8, 31.0, 31.2, 31.7, 37.2, 37.8, 38.4, 39.0, 39.8, 40.4, 40.6, 41.8, 42.3, 49.8, 50.2, 52.2, 52.6, 54.6, 55.2, 57.7, 57.9, 127.6, 128.4, 129.2, 129.6, 129.7, 129.8 d.p 209.5° C.

Example 2

(Use of trifluoroacetic acid (TFA))

(1) Synthesis of D-Phe-D-Phe-D-Leu-D-Lys-Pic-OMe TFA salt (1)

To a 50 mL-recovery flask, TFA (18 mL (18 v/w)), 1-dodecanethiol (1.6 mL (1.6 v/w)), triisopropylsilane (0.2 mL (0.2 v/w)) and H₂O (0.2 mL (0.2 v/w)) were sequentially added and stirred. To the solution, Boc-D-Phe-D-Phe-D-Leu-D-Lys(Boc)-α-Boc-Pic-OMe (9)(1.00 g (1.01 mmol)) was added by a spatula little by little. After completion of the reaction, the mixture was concentrated under reduced pressure by an evaporator and the resultant residue was added dropwise to IPE (20 mL (20 v/w)). The precipitated solid was separated by filtration and the resultant solid was dried under reduced pressure to obtain D-Phe-D-Phe-D-Leu-D-Lys-Pic-OMe.TFA salt (1) (yield 93.0%, HPLC purity 95.2%) as a white solid.

(2) Synthesis of D-Phe-D-Phe-D-Leu-D-Lys-Pic (A)

A 10 mL-recovery flask was charged with D-Phe-D-Phe-D-Leu-D-Lys-Pic-OMe TFA salt (1) (83 mg (0.0843 mmol)), which was dissolved by adding H₂O (431 µL (5.2 v/w)). To the solution, 1N NaOH (345 µL (0.345 mmol)) was added dropwise at room temperature and stirred for 12 hours. After completion of the reaction, 1N HCl (84.3 µL (0.0843 mmol)) was added and concentrated under reduced pressure by an evaporator to obtain D-Phe-D-Phe-D-Leu-D-Lys-Pic (A) (yield quant, HPLC purity 95.4%).

Example 3

(Use of HCl/EtOAc)

(1) A 30 mL-recovery flask was charged with Boc-D-Phe-D-Phe-D-Leu-D-Lys(Boc)-α-Boc-Pic-OMe (9)(1.00 g (1.01 mmol)), which was dissolved by adding EtOAc (7.0 mL (7.0 v/w)). To the solution, 4N HCl/EtOAc (5.0 mL (5.0 v/w)) was added and stirred at room temperature for 24 hours and the precipitated solid was separated by filtration under reduced pressure and washed with EtOAc (2 mL (2.0 v/w)). The resultant solid was dried under reduced pressure to obtain D-Phe-D-Phe-D-Leu-D-Lys-Pic-OMe hydrochloride (1) (781 mg) as a white solid (yield 96.7%, HPLC purity 95.4%).

(2) Synthesis of D-Phe-D-Phe-D-Leu-D-Lys-Pic (A)

A 10 mL-recovery flask was charged with D-Phe-D-Phe-D-Leu-D-Lys-Pic-OMe hydrochloride (1) (90 mg (0.112 mmol)), which was dissolved by adding $H_2O$ (0.47 mL (5.2 v/w)). To the solution, 1N NaOH (459 μL (0.459 mmol)) was added dropwise at room temperature and stirred for 12 hours. After completion of the reaction, 1N HCl (0.112 μL (0.112 mmol)) was added and the mixture was concentrated under reduced pressure by an evaporator to obtain D-Phe-D-Phe-D-Leu-D-Lys-Pic (A) (yield quant, HPLC purity 93.1%).

Example 4

Synthesis of compound by hydrolysis of compound (1) (without purification of compound (1))

A 10 mL-recovery flask was charged with D-Phe-D-Phe-D-Leu-D-Lys-Pic-OMe hydrochloride (1) (114.5 mg (0.142 mmol)) (without purification in the previous step), which was dissolved by adding $H_2O$ (595 μL (5.2 v/w)). To the solution, 1N NaOH (586 μL (0.586 mmol)) was added dropwise at room temperature and stirred for 14 hours. After completion of the reaction, 1N HCl (0.15 μL (0.150 mmol)) was added and concentrated under reduced pressure by an evaporator to obtain D-Phe-D-Phe-D-Leu-D-Lys-Pic (A) (yield quant, HPLC purity 95.2%).

Comparative Example 1

Reaction pathway not via compound (1) (use of Boc-D-Phe-D-Phe-D-Leu-D-Lys(Boc)-α-Boc-Pic-OMe (9) all protected)

(1) Synthesis of Boc-D-Phe-D-Phe-D-Leu-D-Lys(Boc)-α-Boc-Pic-OH

A 30 mL-recovery flask was charged with Boc-D-Phe-D-Phe-D-Leu-D-Lys(Boc)-α-Boc-Pic-OMe (9) (1.00 g (1.00 mmol)), which was dissolved by adding MeOH (5.0 mL (5.0 v/w)). To the solution, 1N NaOH (1.1 mL (1.10 mmol)) was added and stirred at room temperature for 4 days and further, MeOH (5.0 mL (5.0 v/w)) and 1N NaOH (2.0 mL (2.0 mmol)) were added and stirred at 35° C. for 3 hours. After completion of the reaction, 1N HCl (6.1 mL) was added and the mixture was concentrated under reduced pressure to distill off the solvent. Thereafter, EtOAc (5.0 mL (5.0 v/w)) was added and the organic layer was separated. The organic layer was washed by adding NaCl aq. (5.0 mL (5.0 v/w)) and concentrated under reduced pressure to obtain Boc-D-Phe-D-Phe-D-Leu-D-Lys(Boc)-α-Boc-Pic-OH (975.1 mg) (yield 99.3%, HPLC purity 80.8%) as a white solid.

(2) Synthesis of D-Phe-D-Phe-D-Leu-D-Lys-Pic (A)

A 20 mL-recovery flask was charged with Boc-D-Phe-D-Phe-D-Leu-D-Lys(Boc)-α-Boc-Pic-OH (959 mg (0.978 mmol)), which was dissolved by adding EtOAc (4.9 mL (5.0 v/w)). To the solution, 4N HCl/EtOAc (4.9 mL (5.0 mL)) was added dropwise at room temperature and stirred at room temperature for 4 hours. After completion of the reaction, filtration under reduced pressure was carried out to obtain D-Phe-D-Phe-D-Leu-D-Lys-Pic (A) (yield 96.4%, HPLC purity 79.2%) as a white solid.

In the case of a reaction pathway not via the compound (1) of the present invention, the purity of the compound (A) to be obtained was less than 80%.

Example 5

Synthesis of D-Phe-D-Phe-D-Leu-D-Lys-Pic-OMe hydrochloride (1))

A reaction was carried out in the same manner as in Example 1 (8) by replacing the reaction solvent IPA (1.65 v/w) as shown in Table 1 (solvent and amount). The results are shown in Table 1.

TABLE 1

|  |  | IPA/MeCN | IPA/THF | IPA/MeCN | IPA/toluene | IPA/THF |
|---|---|---|---|---|---|---|
| Boc removal reaction | Solvent | | | | | |
| | Solvent ratio | (50:50) | (50:50) | (50:50) | (50:50) | (50:50) |
| | Liquid amount | 10 v/w | 10 v/w | 20 v/w | 20 v/w | 20 v/w |
| | Purity | 97.1% | 97.4% | 98.4% | 98.3% | 97.0% |
| | Yield | 90% | 88% | 84% | 101% | 96% |

Example 6

Purification of D-Phe-D-Phe-D-Leu-D-Lys-Pic-OMe hydrochloride (1))

A reaction was carried out in the same manner as in Example 1 (9) by replacing the purification solvent EtOH/MeCN (16.7:83.5, 20 v/w) as shown in Table 2 (solvent and amount). The results are shown in Table 2.

TABLE 2

| | Solvent | MeCN | toluene | THF | acetone | EtOH/MeCN | IPA/MeCN | IPA/toluene | IPA/THF |
|---|---|---|---|---|---|---|---|---|---|
| Slurry purification | Solvent ratio | 100 | 100 | 100 | 100 | (16.7:83.5) | (50:50) | (50:50) | (50:50) |
| | Liquid amount | 10 v/w | 10 v/w | 10 v/w | 10 v/w | 10 v/w | 13 v/w | 13 v/w | 13 v/w |
| | Purity | 98.9% | 98.9% | 99.0% | 99.1% | 99.1% | 99.0% | 98.5% | 98.1% |
| | Yield | 78% | 93% | 84% | 90% | 83% | 87% | 93% | 93% |

The invention claimed is:

1. A compound represented by the following formula (1) or a salt thereof:

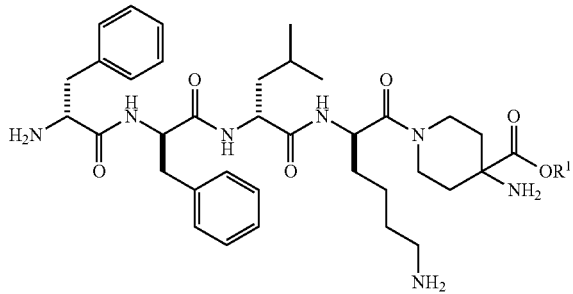

(1)

wherein $R^1$ represents an alkyl group or an aralkyl group.

2. The compound or a salt thereof according to claim 1, wherein $R^1$ is an alkyl group.

3. The compound or a salt thereof according to claim 1, wherein the compound or a salt thereof is an acid addition salt of the compound.

4. A method of producing a compound represented by formula (A) or a salt thereof:

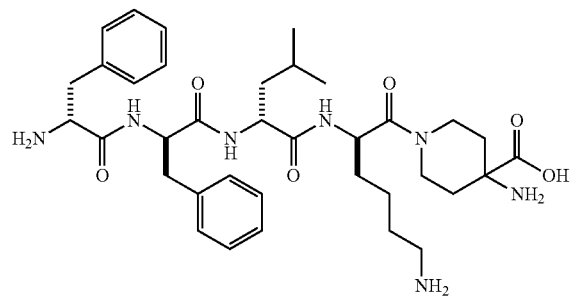

(A)

comprising hydrolyzing the compound or a salt thereof according to claim 1.

5. The compound or a salt thereof according to claim 1, wherein $R^1$ is an aralkyl group.

6. The compound or a salt thereof according to claim 1, wherein $R^1$ is a linear alkyl group having 1 to 12 carbon atoms.

7. The compound or a salt thereof according to claim 1, wherein $R^1$ is a branched alkyl group having 1 to 12 carbon atoms.

8. The compound or a salt thereof according to claim 1, wherein $R^1$ is a linear alkyl group having 1 to 8 carbon atoms.

9. The compound or a salt thereof according to claim 1, wherein $R^1$ is a branched alkyl group having 1 to 8 carbon atoms.

10. The compound or a salt thereof according to claim 1, wherein $R^1$ is a linear alkyl group having 1 to 4 carbon atoms.

11. The compound or a salt thereof according to claim 1, wherein $R^1$ is a branched alkyl group having 1 to 4 carbon atoms.

12. The compound or a salt thereof according to claim 1, wherein $R^1$ is an alkyl group selected from the group consisting of methyl, ethyl, n-propyl, isopropyl, n-butyl and tert-butyl.

13. The compound or a salt thereof according to claim 1, wherein $R^1$ is methyl.

14. The compound or a salt thereof according to claim 1, wherein $R^1$ is an aralkyl group having 7 to 18 carbon atoms.

15. The compound or a salt thereof according to claim 1, wherein $R^1$ is an aralkyl group that is a $C_{6-14}$ aryl-$C_{1-4}$ alkyl group.

16. The compound or a salt thereof according to claim 1, wherein $R^1$ is an aralkyl group that is a phenyl-$C_{1-4}$ alkyl group.

17. The compound or a salt thereof according to claim 1, wherein $R^1$ is a benzyl group.

18. The compound or salt thereof according to claim 3, which is an acid addition salt selected from the group consisting of a hydrochloride, a sulfate, a nitrate, an acetate and a trifluoroacetate.

* * * * *